United States Patent [19]
Anderson et al.

[11] Patent Number: 5,985,322
[45] Date of Patent: *Nov. 16, 1999

[54] METHOD FOR THE TREATMENT OF CNS DISORDERS

[75] Inventors: Neil R. Anderson, West Lafayette; Roger F. Harrison, Zionsville; Daniel F. Lynch, Indianapolis; Peter L. Oren, Fishers, all of Ind.

[73] Assignee: Eli Lilly and Company, Indianapolis, Ind.

[*] Notice: This patent is subject to a terminal disclaimer.

[21] Appl. No.: 09/265,610

[22] Filed: Mar. 10, 1999

Related U.S. Application Data

[62] Division of application No. 08/867,196, May 29, 1997, Pat. No. 5,910,319.

[51] Int. Cl.$^6$ .................................................. A61K 9/54
[52] U.S. Cl. .................... 424/458; 424/459; 424/461; 424/463; 424/464; 424/489; 514/962; 514/646
[58] Field of Search .................... 424/489, 458, 424/461, 490, 494, 459, 464, 465; 514/962, 646

[56] References Cited

U.S. PATENT DOCUMENTS

| | | |
|---|---|---|
| 4,314,081 | 2/1982 | Molloy et al. . |
| 4,444,778 | 4/1984 | Coughlin . |
| 4,626,549 | 12/1986 | Molloy et al. . |
| 4,847,092 | 7/1989 | Thakkar et al. . |
| 5,104,899 | 4/1992 | Young et al. . |
| 5,356,934 | 10/1994 | Robertson et al. . |
| 5,508,276 | 4/1996 | Anderson et al. . |

FOREIGN PATENT DOCUMENTS

| | | | |
|---|---|---|---|
| 687472 | 12/1995 | European Pat. Off. | ........ A61K 45/06 |
| 693281 | 1/1996 | European Pat. Off. | ...... A61K 31/135 |
| 92/13452 | 8/1992 | WIPO | ............. A01N 43/60 |
| 92/19226 | 11/1992 | WIPO | .............. A61K 9/16 |
| 93/18755 | 9/1993 | WIPO | .............. A61K 9/16 |
| 93/24154 | 12/1993 | WIPO | ............. A61L 15/62 |
| 95/12385 | 5/1995 | WIPO | ............. A61K 9/107 |

OTHER PUBLICATIONS

Montgomery, et al., *Eur. Arch. Psychiatry Clin. Neurosci.*, 244:211–215 (1994).
Burke, et al., *Psychopharmacol. Bull.* 31 (3); 524 (1995).
Stafford, et al., *Drug Development and Industrial Pharmacy*, 8(4) :513–530 (1982).
Osterwald, Hermann P., *Pharmaceutical Research*, 2:14–18 (1985).
Davis, et al., *Drug Development and Industrial Pharmacy*, 12(10):1419–1448 (1986).
Bloor, et al., *Drug Development and Industrial Pharmacy*, 15 (15–16) :2227–2243.
Nagai, et al., *Aqueous Polymeric Coating for Pharmaceutical Dosage Forms*, Marcel Dekker, N.W. and Basel, 81–152 (1989).
Chang, Rong–Kun, *Pharmaceutical Technology*, 14(10) :2–70 (1990).
Fujii, et al., Recent Advances On Aqueous Polymeric Coating System and Related Techniques, Proceedings of Pre–World Congress Particle Technology in Gifu, Sep. 17–18, 1990, Gifu,Japan, 80–85 (1990).
Delattre, et al., Proceed. Intern. Symp. Control. Rel. Bioact. Mater., 19:267–268 (1992).
Schmidt, et al., *Drug Development and Industrial Pharmacy*, 18(18) :1969–1979 (1992).
Wyatt "Enhanced Stability of Aqueous Cellulose Acetate Phthalate (CAP) Enteric Films." Presented AAPS Annual Meeting, San Antonio, TX, Nov. 15–19, 1992.
Takahata, et al., *Chemical and Pharmaceutical Bulletin*, 41(6) :1137–1143 (1993).
Obara, et al., *Pharmaceutical Research*, 11(11) :1562–1567 (1994).
Shin–Etsu Chemical CO., Ltd., "An Improved Aqueous Coating using Shin–Etsu AQOAT", AQOAT Technical Information Bulletin, 1994.
Japan Pharmaceutical Excipients Council, "Hydroxypropylmethylcellulose Acetate Succinate", Japanese Pharmaceutical Excipients 1993 (JPE 1993), 183–187, Yakuji Nippo, Ltd., Tokyo, Japan, 1994.
Shin–Etsu Chemical Co., Ltd. "Dry Coating", AQOAT Technical Inormation No. A–3, Sep., 1996.
Obara, et al., Poster PT6115, Dry Coating—A Novel.

*Primary Examiner*—Thurman K. Page
*Assistant Examiner*—Brian K. Seidleck
*Attorney, Agent, or Firm*—Robert D. Titus; Robert A. Conrad

[57] ABSTRACT

An improved method for the treatment of central nervous system disorders comprises treating patients with an enteric fluoxetine formulation.

10 Claims, No Drawings

METHOD FOR THE TREATMENT OF CNS DISORDERS

CROSS REFERENCE

This application is a divisional of Ser. No. 08/867,196, filed on May 29, 1997 now U.S. Pat. No. 5,910,319.

FIELD OF THE INVENTION

This invention belongs to the field of pharmaceutical science, and provides a superior enteric formulation of the anti-depressant drug, fluoxetine.

BACKGROUND OF THE INVENTION

Fluoxetine (N-methyl-3-(p-trifluoromethylphenoxy)-3-phenylpropylamine) is an antidepressant drug which is disclosed, for example, in U.S. Pat. Nos. 4,314,081 and 4,626,549. The action of fluoxetine is based on its capacity to selectively inhibit the uptake of serotonin by the neurons in the central nervous system. Fluoxetine is indicated in the U.S. and many other countries for the treatment of depression, obsessive-compulsive disorder, and bulimia.

In the U.S., the currently available pharmaceutical forms for fluoxetine, in the form of the hydrochloride salt, include capsules and a solution. A tableted formulation for compounds of the fluoxetine type is also contemplated in U.S. Pat. No. 4,314,081 (column 16, lines 52–55). More recently, a dispersible tablet has been disclosed (see EPO Patent application publication 693,281). A sustained release formulation of fluoxetine is claimed in U.S. Pat. No. 4,847,092. Tablets of serotonin uptake inhibitors which are coated to delay absorption and disintegration to "provide a sustained action over a longer period" are generally contemplated in U.S. Pat. No. 4,444,778 (column 6, line 10 et seq.). Formulations of R-fluoxetine are generally contemplated in WO 92/13452 (controlled release and sustained release—page 19) and U.S. Pat. No. 5,356,934 (column 4). Similar teaching for S-fluoxetine are found in U.S. Pat. No. 5,104,899.

Enteric pharmaceutical formulations are manufactured in such a way that the product passes unchanged through the stomach of the patient, and dissolves and releases the active ingredient quickly when it leaves the stomach and enters the small intestine. Such formulations have long been used, and conventionally are in tablet or pellet form, where the active ingredient is in the inner part of the tablet or pellet and is enclosed in a film or envelope, the "enteric coating", which is insoluble in acid environments, such as the stomach, but is soluble in near-neutral environments such as the small intestine.

Certain difficulties arose in preparing conventional enteric formulations of fluoxetine. In particular, fluoxetine was found to react with many enteric coatings to form a slowly- or even insoluble coating. Similar reactions with enteric coatings have been observed with other drugs—duloxetine, nortriptyline, desipramine, sertraline and paroxetine.

Duloxetine, undergoing clinical evaluation as a candidate antidepressant, is (+)-N-methyl-3-(1-naphthalenyloxy)-2-thiophenepropanamine, and is commonly used as its hydrochloride salt. An enteric coated formulation of duloxetine is claimed in U.S. Pat. No. 5,508,276, to avoid acid degradation of the compound in the stomach.

It has been observed that, because of fluoxetine's long half life, dosing regimens other than daily dosing are effective, especially for maintenance dosing. For example, Burke, et al., *Psychopharmacol. Bull.*, 31(3), 524 (1995) reported that 60 mg of fluoxetine hydrochloride given once per week was as effective as 20 mg per day during maintenance therapy (i.e., after eight weeks of daily dosing). Montgomery, et al., *Eur. Arch. Psychiatry Clin. Neuroscience*, 244(4), 211 (1994) reported that 120 mg of fluoxetine dosed biweekly was ineffective for treating recurrent brief depression. Twenty milligrams per week of fluoxetine were advocated by Benazzi, et al., *Pharmacopsychiatry*, 27(6), 246 (1994), for reducing sexual dysfunction side effects. While the above studies employed single or multiple 20 mg capsules to provide the indicated therapy, 60 mg capsules of fluoxetine hydrochloride are available in, e.g., South Africa for treating bulimia.

Because of fluoxetine's long half life, there has not been any perceived need to actually prepare a fluoxetine formulation providing a longer payout. While these higher doses of fluoxetine have been shown to be efficacious, there can be associated side effects, such as nausea, presumably due to local irritation or the increased plasma levels shortly after dosing. Therefore, it has now been appreciated that a formulation having higher doses of fluoxetine (e.g., 60–120 mg) which blunts the initial release of fluoxetine will have clinical advantages, i.e., not only will such formulations provide convenient and effective one per week dosing, but will have an advantage of less side effects.

It is therefore desirable to have a formulation that could be used to provide a convenient single dose for maintenance therapy suggested by the above articles without providing an increase in undesirable side effects.

The present invention was created through efforts to solve the above and other problems, and provides a superior enteric formulation of fluoxetine.

SUMMARY OF THE INVENTION

The present invention provides an enteric fluoxetine pellet comprising a) a core consisting of fluoxetine and one or more pharmaceutically acceptable excipients; b) an optional separating layer; c) an enteric layer comprising hydroxypropyl-methylcellulose acetate succinate (HPMCAS) and a pharmaceutically acceptable excipient; d) an optional finishing layer.

The invention also provides a method of manufacturing an enteric fluoxetine pellet comprising a) providing a core consisting of fluoxetine and one or more pharmaceutically acceptable excipients; b) optionally, applying to the core a separating layer comprising one or more pharmaceutically acceptable excipients; c) applying an enteric layer comprising HPMCAS and one or more pharmaceutically acceptable excipients, wherein the HPMCAS is applied as an aqueous solution or suspension and the application takes place in an apparatus of the fluid bed type; d) optionally, applying a finishing layer.

DETAILED DESCRIPTION AND PREFERRED EMBODIMENTS

Throughout the present document, all expressions of percentage, ratio, proportion and the like, will be in weight units unless otherwise stated. Expressions of proportions of the enteric product will refer to the product in dried form, after the removal of the water in which many of the ingredients are dissolved or dispersed.

This invention contemplates formulations containing fluoxetine preferably as the hydrochloride salt—however, as will be appreciated by skilled artisans, other salt forms or the free base form could be used to obtain the same beneficial effect provided by this invention. Moreover, solvates of fluoxetine or its salts as well as the free base, salts, and/or solvates of the individual isomers of fluoxetine, namely R-fluoxetine and S-fluoxetine, are contemplated by this invention (see, e.g., Robertson, et al., *J. Med. Chem.*, 31, 1412 (1988)). Throughout this description, unless specified otherwise, the term "fluoxetine" contemplates all such forms, although fluoxetine hydrochloride is clearly the most preferred embodiment of this invention.

When used in this description, the term "sugar" refers to a sugar other than a reducing sugar. A reducing sugar is a carbohydrate that reduces Fehling's (or Benedict's) or Tollens' reagent. All monosaccharides are reducing sugars as are most disaccharides with the exception of sucrose. One common sugar used frequently as a binding or filling agent is lactose. This excipient is particularly useful for tablets since it compresses well, is both a diluent and binder, and is cheap. However, it is a reducing sugar and it has been discovered that over time fluoxetine interacts with lactose both at room temperature and under accelerated stability conditions (heat). Therefore, avoidance of lactose and other reducing sugars from formulations comprising fluoxetine is critical to this invention. As discussed below, sucrose is a preferred sugar.

The various components and layers of the pellet will be individually discussed as follows, together with the methods of adding the different ingredients to build up the fluoxetine pellet.

The Core

A preferred core for the pellet is prepared by applying a fluoxetine-containing layer to an inert core. Such inert cores are conventionally used in pharmaceutical science, and are readily purchased in all industrial countries. The most preferred core is one prepared from starch and sucrose, for use in confectionery as well as in pharmaceutical manufacturing. However, cores of any pharmaceutically acceptable excipient may be used, including, for example, microcrystalline cellulose, vegetable gums, waxes, and the like. The primary characteristic of the inert core is to be inert, with regard both to fluoxetine and the other excipients in the pellet and with regard to the patient who will ultimately ingest the pellet.

The size of the cores depends, of course, on the desired size of the pellet to be manufactured. In general, pellets can be as small as 0.1 mm, or as large as 2 mm. Preferred cores are from about 0.3 to about 0.8 mm, in order to provide finished pellets in the desired preferred size range of from about 0.5 to about 1.5 mm in diameter.

It is always preferred for the cores to be of a reasonably narrow particle size distribution, in order to improve the uniformity of the various coatings to be added and the homogeneity of the final product. For example, the cores may be specified as being of particle size ranges such as from 18 to 20 U.S. mesh, from 20 to 25 U.S. mesh, from 25 to 30 U.S. mesh, or from 30 to 35 U.S. mesh to obtain acceptable size distributions of various absolute sizes.

The amount of cores to be used obviously depends on the weights and thicknesses of the added layers; in general, the cores comprise from about 10 to about 70 percent of the product. More preferably, the charge of cores represents from about 15 to about 45 percent of the product.

When manufacture of the pellet begins with inert cores, the fluoxetine is coated on the cores to yield a final drug concentration of about 10 to about 25 percent of the product, in general. The amount of fluoxetine, of course, depends on the desired dose of the drug and the quantity of pellets which it is desired to administer. The dose of fluoxetine is in the range of 20–100 mg (base equivalent), more usually 80–90 mg, and the usual amount of pellets is that amount which is conveniently held in gelatin capsules. Comparison of the volume of gelatin capsules and the desired doses leads the pharmacist to the concentration range of from about 15% to about 25% of fluoxetine in the present product.

Some attention must be given to the particle size of fluoxetine. The compound can precipitate in needle-like crystals which can be quite large. Coating cores with fluoxetine in the large needle-like form can be difficult, and it is advisable to mill or otherwise reduce the particle size of the fluoxetine to less than about 50 $\mu$m before using it in the present product and process.

A convenient manner of coating the cores with fluoxetine is the "powder coating" process where the cores are moistened with a sticky liquid or binder, fluoxetine is added as a powder, and the mixture is dried. Such a process is regularly carried out in the practice of industrial pharmacy, and suitable equipment is in daily use.

Such equipment is, in fact, used in several steps of the present process, and it will, accordingly, be discussed in detail here. Historically, this process has been conducted in conventional coating pans similar to those employed in sugar coating processes. This process can be used to prepare pellets, but this equipment has less efficient air flow and drying capabilities which limits application rates and can result in longer processing times in order to minimize agglomerations.

Alternately, the present product could be made in fluidized bed equipment (using a rotary processor), or in rotating plate equipment such as the Freund CF-Granulator (Vector Corporation, Marion, Iowa). The rotating plate equipment typically consists of a cylinder, the bottom of which is a rotatable plate. Motion of the mass of particles to be coated is provided by friction of the mass between the stationary wall of the cylinder and the rotating bottom of it. Means can be provided to apply warm air to dry the mass, and liquids can be sprayed on the mass and balanced against the drying rate as in the fluidized bed case.

When a powder coating is to be applied, the mass of pellets, in the present case, is maintained in a sticky state, and the powder to be adhered to them, fluoxetine in this case, is added continuously or periodically and adheres to the sticky pellets. When all of the fluoxetine has been applied, the spray is stopped and the mass is allowed to dry in the air stream. It may be appropriate or convenient to add some inert powders to the fluoxetine.

Additional solids may be added to the layer with fluoxetine. These solids may be added to facilitate the coating process as needed to aid flow, reduce static charge, aid bulk buildup and form a smooth surface. Inert substances such as talc, kaolin, and titanium dioxide, lubricants such as magnesium stearate, finely divided silicon dioxide, crospovidone, and non-reducing sugars, e.g., sucrose, may be used. The amounts of such substances are in the range from about a few tenths of 1% of the product, up to about 20% of the product. Such solids should be of fine particle size, less than 50 $\mu$m, to produce a smooth surface.

The fluoxetine is made to adhere to the cores by spraying a pharmaceutical excipient which is sticky and adherent when it is wet, and dries to a strong, coherent film. Pharmaceutical scientists are aware of and conventionally use many such substances, most of them polymers. Preferred such polymers include hydroxypropylmethylcellulose, hydroxypropyl-cellulose and polyvinylpyrrolidone. Additional such substances include methylcellulose, carboxymethylcellulose, acacia and gelatin, for example. The amount of the adhering excipient is in the range from about 4% to about 12% of the product, and depends in large part on the amount of fluoxetine to be adhered to the core.

Fluoxetine may also be built up on the cores by spraying a slurry comprising fluoxetine suspended in a solution of the excipients of the fluoxetine layer, dissolved or suspended in sufficient water to make the slurry sprayable. Such a slurry may be milled through a machine adapted for grinding suspensions in order to reduce the particle size of fluoxetine. Grinding in suspension form is desirable because it avoids dust generation and containment problems which arise in grinding dry powder drugs. A preferred method for applying this suspension is in the classic pharmaceutical fluidized bed coating device, such as the Wurster column, which consists simply of a vertical cylinder with an air-permeable bottom and an upward spraying nozzle close above the bottom, or a downward-spraying nozzle mounted above the product mass. The cylinder is charged with particles to be coated, sufficient volume of air is drawn through the bottom of the cylinder to suspend the mass of particles, and the liquid to be applied is sprayed onto the mass. The temperature of the fluidizing air is balanced against the spray rate to maintain the mass of pellets or tablets at the desired level of moisture and stickiness while the coating is built up.

On the other hand, the core may comprise a monolithic particle in which the fluoxetine is incorporated. Such cores may be prepared by the granulation techniques which are wide spread in pharmaceutical science, particularly in the preparation of granular material for compressed tablets. The particle size of the cores is too small for preparation by compression techniques, but the cores may be prepared by mixing the fluoxetine into a mass of pharmaceutical excipients, moistening the mass with water or a solvent, drying, and breaking the mass into sized particles in the same size range as described above for the inert cores. This can be accomplished via the process of extrusion and marumerization.

The core for the pellet can also be prepared by mixing fluoxetine with conventional pharmaceutical ingredients to obtain the desired concentration and forming the mixture into cores of the desired size by conventional procedures or by the process of R. E. Sparks, et al., U.S. Pat. Nos. 5,019,302 and 5,100,592, incorporated by reference herein.

Separating Layer

The separating layer between the fluoxetine-containing core and the enteric layer is not required, but is a preferred feature of the formulation. The functions of the separating layer, if required, are to provide a smooth base for the application of the enteric layer, to prolong the pellet's resistance to acid conditions, and to improve stability by inhibiting any interaction between the drug and the enteric polymer in the enteric layer.

The smoothing function of the separating layer is purely mechanical, the objective of which is to improve the coverage of the enteric layer and to avoid thin spots in it, caused by bumps and irregularities on the core. Accordingly, the more smooth and free of irregularities the core can be made, the less material is needed in the separating layer, and the need for the smoothing characteristic of the separating layer may be avoided entirely when the fluoxetine is of extremely fine particle size and the core is made as close as possible to truly spherical.

It has been found that, when a pharmaceutically acceptable non-reducing sugar is added to the separating layer, the pellet's resistance to acid conditions is markedly and surprisingly increased. Accordingly, such a sugar may be included in the separating layer applied to the cores, either as a powdered mixture, or dissolved as part of the sprayed-on liquid. A sugar-containing separating layer can reduce the quantity of enteric polymer required to obtain a given level of acid resistance. It therefore considerably reduces the expense of the present formulated product. Use of less enteric polymer reduces both the materials cost and processing time, and also reduces the amount of polymer available to react with fluoxetine. The inhibition of any core/enteric layer interaction is mechanical. The separating layer physically keeps the components in the core and enteric layers from coming into direct contact with each other. In some cases, the separating layer can also act as a diffusional barrier to migrating core or enteric layer components dissolved in product moisture. The separating layer can also be used as a light barrier by opacifying it with agents such as titanium dioxide, iron oxides and the like.

In general, the separating layer is composed of coherent or polymeric materials, and finely powdered solid excipients which constitute fillers. When a sugar is used in the separating layer, it is applied in the form of an aqueous solution and constitutes part of or the whole of the coherent material which sticks the separating layer together. In addition to or instead of the sugar, a polymeric material may also be used in the separating layer. For example, substances such as hydroxypropylmethylcellulose, polyvinylpyrrolidone, hydroxypropylcellulose and the like may be used in small amounts to increase the adherence and coherence of the separating layer.

It is further advisable to use a filler excipient in the separating layer to increase the smoothness and solidity of the layer. Substances such as finely powdered talc, silicon dioxide and the like are universally accepted as pharmaceutical excipients and may be added as is convenient in the circumstances to fill and smooth the separating layer.

In general, the amount of sugar in the separating layer may be in the range of from about 2% to about 10% of the product, when a sugar is used at all, and the amount of polymeric or other sticky material may be in the range of from about 0.1 to about 5%. The amount of filler, such as talc, should be in the range of from about 5 to about 15%, based on final product weight.

The separating layer may be applied by spraying aqueous solutions of the sugar or polymeric material, and dusting in the filler as has been described in the preparation of a fluoxetine layer. The smoothness and homogeneity of the separating layer can be improved, however, if the filler is thoroughly dispersed as a suspension in the solution of sugar and/or polymeric material, and the suspension is sprayed on the core and dried, using equipment as described above in the preparation of cores with fluoxetine layers.

Enteric Layer

The enteric layer is comprised of an enteric polymer, which must be chosen for compatibility with fluoxetine as discussed above. The polymer must be one having only a small number of carboxylic acid groups per unit weight or repeating unit of the polymer. The preferred enteric polymer is hydroxypropylmethylcellulose acetate succinate (HPMCAS), which product is defined as containing not less than 4% and not more than 28% of succinoyl groups, which are the only free carboxylic groups in the compound. See Japanese Standards of Pharmaceutical Ingredients 1991, page 1216–21, Standard No. 19026. HPMCAS is available from Shin-Etsu Chemical Co., Ltd., Tokyo, Japan, under the trademark AQOAT. It is available in two particle size grades and three molecular weight ranges. The L grade, having number average molecular weight of 93,000, is used in the present examples but other grades are expected to be usable.

Enteric polymers may be applied as coatings from aqueous suspensions, from solutions in aqueous or organic solvents, or as a powder. Application from organic solvents is presently not at all favored in the pharmaceutical industry, because of the cost of the solvent and the difficulty in either disposing of solvent vapors or recovering the evaporated solvent. Accordingly, no detailed discussion of application of the enteric layer from organic solvents will be given here, but the pharmaceutical scientist will recognize that such application is entirely possible if circumstances favor it.

The enteric polymer can also be applied according to a method described by Shin-Etsu Chemical Co. Ltd. (Obara, et al., Poster PT6115, AAPS Annual Meeting, Seattle, Wash., Oct. 27–31, 1996). When the enteric polymer is applied as a powder the enteric polymer is added directly in the solid state to the tablets or pellets while plasticizer is sprayed onto the tablets or pellets simultaneously. The deposit of solid enteric particles is then turned into a film by curing. The curing is done by spraying the coated tablets or pellets with a small amount of water and then heating the tablets or pellets for a short time. This method of enteric coating application can be performed employing the same type of equipment as described above in the preparation of cores with fluoxetine layers When the enteric polymer is applied as an aqueous suspension, a problem in obtaining a uniform, coherent film often results. It is very advisable, accordingly, to purchase a fine particle grade or grind the particles of polymer to an extremely small size before application. It is possible either to grind the dry polymer, as in an air-impaction mill or to prepare the suspension and grind the polymer in slurry form. Slurry grinding is generally preferable, particularly since it can be used also to grind the filler portion of the enteric layer in the same step. It is advisable to reduce the average particle size of the enteric polymer to the range from about 1 μm to about 5 μm, preferably no larger than 3 μm.

When the enteric polymer is applied in the form of a suspension, it is important to assure that the suspension remains homogeneous, and that conditions which favor the agglomeration of the polymer do not occur. Such precautions include maintaining the suspension in a gently stirred condition, but not stirring so vigorously as to create foam, and assuring that the suspension does not stand still in eddies in nozzle bodies, for example, or in over-large delivery tubing. Frequently polymers in suspension form will agglomerate if the suspension becomes too warm, and the critical temperature may be as low as 30° C. in individual cases. Since spray nozzles and tubing are exposed to hot air in the usual fluid bed type equipment, care must be taken to assure that the suspension is kept moving briskly through the equipment to cool the tubing and nozzle. When HPMCAS is used, in particular, it is advisable to cool the suspension below 20° C. before application, to cool the tubing and nozzle by pumping a little cold water through them before beginning to pump the suspension, and to use supply tubing with as small a diameter as the spray rate will allow so that the suspension can be kept moving rapidly in the tubing.

It is preferred in the present invention, however, to apply the enteric polymer as an aqueous solution whenever it is possible to do so. In the case of HPMCAS, dissolution of the polymer can be obtained by neutralizing the polymer, preferably with ammonia. Neutralization of the polymer may be obtained merely by adding ammonia, preferably in the form of aqueous ammonium hydroxide to a suspension of the polymer in water; complete neutralization results in complete dissolution of the polymer at about pH 5.7–5.9. Good results are also obtained when the polymer is partially neutralized, by adding less than the equivalent amount of ammonia. In such case, the polymer which has not been neutralized remains in suspended form, suspended in a solution of neutralized polymer. As noted earlier, it is obviously important to control the particle size of the polymer when such a process is to be used. Use of neutralized polymer more readily provides a smooth, coherent enteric layer than when a suspended polymer is used, and use of partially neutralized polymer provides intermediate degrees of smoothness and coherency. Particularly when the enteric layer is applied over a very smooth separating layer, excellent results may be obtained from partially neutralized enteric polymer.

The extent of neutralization may be varied over a range without adversely affecting results or ease of operation. For example, operation with from about 25% to about 100% neutralization is preferred in the present invention. Another preferred condition is from about 45% to about 100% neutralization, and another preferred condition is from about 65% to about 100%. Still another preferred manner of neutralization is from about 25% to about 65% neutralized. It is found, however, that the enteric polymer in the resulting product, after drying, is neutralized to a lesser extent than when applied. When neutralized or partially neutralized HPMCAS is applied, the HPMCAS in the final product is from about 0% to about 25% neutralized, more preferably from about 0% to about 15% neutralized.

Most enteric polymers require the addition of a plasticizer for best results. In the case of HPMCAS, the preferred plasticizer is triethyl citrate, used in an amount up to about 15–30% of the amount of enteric polymer in aqueous suspension application. When a neutralized HPMCAS is employed, lower levels or no plasticizer may be required.

Minor ingredients, such as antifoam, suspending agents when the polymer is in suspended form, and surfactants to assist in smoothing the film are also commonly used. For example, silicone anti-foams, surfactants such as polysorbate 80, sodium lauryl sulfate and the like and suspending agents such as carboxymethylcellulose, vegetable gums and the like may commonly be used at amounts in the general range up to 1% of the product.

Usually, an enteric layer is filled with a powdered excipient such as talc, glyceryl monostearate or hydrated silicon dioxide to build up the thickness of the layer, to strengthen it, to reduce static charge, and to reduce particle cohesion. Amounts of such solids in the range of from about 1% to about 10% of the final product may be added to the enteric polymer mixture, while the amount of enteric polymer itself is usually in the range from about 5% to about 25%, more preferably, from about 10% to about 20%.

Application of the enteric layer to the pellets follows the same general procedure previously discussed, using fluid bed type equipment with simultaneous spraying of enteric polymer solution or suspension and warm air drying. Temperature of the drying air and the temperature of the circulating mass of pellets should be kept in the ranges advised by the manufacturer of the enteric polymer.

Finishing Layer

A finishing layer over the enteric layer is not necessary in every case, but frequently improves the elegance of the product and its handling, storage and machinability and may provide further benefits as well. The simplest finishing layer is simply a small amount, about less than 1% of an anti-static ingredient such as talc or silicon dioxide, simply dusted on the surface of the pellets. Another simple finishing layer is a small amount, about 1%, of a wax such as beeswax melted onto the circulating mass of pellets to further smooth the pellets, reduce static charge, prevent any tendency for pellets to stick together, and increase the hydrophobicity of the surface.

More complex finishing layers may constitute a final sprayed-on layer of ingredients. For example, a thin layer of polymeric material such as hydroxypropylmethylcellulose, polyvinylpyrrolidone and the like, in an amount such as from about 2% up to about 10%, may be applied. The polymeric material may also carry a suspension of an opacifier, a bulking agent such as talc, or a coloring material, particularly an opaque finely divided color agent such as red or yellow iron oxide. Such a layer quickly dissolves away in the stomach, leaving the enteric layer to protect the fluoxetine, but provides an added measure of pharmaceutical elegance and protection from mechanical damage to the product.

Finishing layers to be applied to the present product are of essentially the same types commonly used in pharmaceutical science to smooth, seal and color enteric products, and may be formulated and applied in the usual manners.

The following Examples set out the preparation of a number of different enteric granules within the concept of the present invention. The Examples are intended further to enlighten the reader about the present enteric pellets and their methods of manufacture; additional variations within the concept of the invention will be clear to the pharmaceutical scientist and their preparation will be within the scientist's competence.

For each example, a bill of materials will first be given, which will be expressed in terms of the amount of each ingredient used to prepare a single unit dose of the granules. Following the bill of materials, the process will be described, giving the equipment and the batch size used in the various stages of manufacture.

EXAMPLE 1

90 mg Fluoxetine base/capsule

| Bill of Materials | |
|---|---|
| Cores | |
| Sucrose - starch nonpareils, 30–35 mesh | 134.15 mg |
| Fluoxetine layer | |
| Fluoxetine | 100.58 mg |
| Sucrose | 25.72 mg |
| Hydroxypropylmethylcellulose | 12.89 mg |
| Separating layer | |
| Hydroxypropylmethylcellulose | 9.45 mg |
| Sucrose | 28.24 mg |
| Talc, 500 mesh | 50.21 mg |
| Enteric layer | |
| HPMCAS-LF | 65.66 mg |
| Triethyl citrate | 13.14 mg |
| Talc, 500 mesh | 19.66 mg |
| Finishing Layer | |
| Color mixture white (HPMC + titanium dioxide) | 43.02 mg |
| HPMC | 10.78 mg |
| Talc | Trace |
| | 513.50 mg |

The fluoxetine layer was built up by suspending fluoxetine hydrochloride 25% w/w in a binder solution consisting of 6.4% w/w sucrose and 3.2% w/w hydroypropyl methylcellulose (HPMC). The resulting suspension was then passed through a Coball Mill (Fryma Mashinen AG, Rheinfelden, Switzerland) model MS-12 to reduce the particle size of the bulk drug. The milled suspension was applied to 1.5 kg of sucrose starch non-pareils in a fluid bed dryer which had been fitted with a Wurster column. Upon completing the application of the desired quantity of fluoxetine hydrochloride suspension, the fluoxetine core pellets were completely dried in the fluid bed dryer.

The separating layer which consisted of talc 12% w/w, sucrose 6.75% w/w and hydroxypropyl methylcellulose 2.25% w/w was then applied as an aqueous suspension to the fluoxetine core pellets. Upon completing the application of the desired quantity of suspension, the pellets were completely dried in the fluid bed dryer.

The enteric coating aqueous suspension consisted of hydroxypropyl methylcellulose acetate succinate type LF 6% w/w, talc 1.8% w/w, triethyl citrate 1.2% w/w which was fully neutralized by the addition of 0.47% w/w ammonium hydroxide. This enteric coating suspension was applied to the fluoxetine separation layer coated pellets. Upon completing the application of the desired quantity of enteric coating suspension, the pellets were completely dried in the fluid bed dryer and a small quantity of talc was added to reduce static charge.

A finishing layer was then applied which consisted of color mixture white (comprised of titanium dioxide and hydroxypropyl methylcellulose) 8% w/w and hydroxypropyl methylcellulose 2% w/w. Upon completing the application of the desired quantity of color coating suspension, the pellets were completely dried in the fluid bed dryer and a small quantity of talc was added to reduce static charge. The resulting pellets were assayed for fluoxetine content and filled into capsules to provide 90 mg of fluoxetine base.

EXAMPLE 2

90 mg Fluoxetine base/capsule

| Bill of Materials | |
|---|---|
| Cores | |
| Sucrose - starch nonpareils, 30–35 mesh | 134.19 mg |
| Fluoxetine layer | |
| Fluoxetine hydrochloride | 100.62 mg |
| Sucrose | 25.77 mg |
| Hydroxypropylmethylcellulose | 12.89 mg |
| Separating layer | |
| Hydroxypropylmethylcellulose | 6.12 mg |
| Sucrose | 18.27 mg |
| Talc, 500 mesh | 32.49 mg |
| Enteric layer | |
| HPMCAS-LF | 74.89 mg |
| Triethyl citrate | 14.96 mg |
| Talc, 500 mesh | 21.77 mg |
| Finishing layer | |
| Color mixture white (HPMC + titanium dioxide) | 43.02 mg |
| HPMC | 10.78 mg |
| Talc | Trace |
| | 493.65 mg |

The product was made substantially according to the process used in Example 1.

EXAMPLE 3

90 mg Fluoxetine base/capsule

| Bill of Materials | |
|---|---|
| Cores | |
| Sucrose - starch nonpareils, 30–35 mesh | 121.01 mg |
| Fluoxetine layer | |
| Fluoxetine hydrochloride | 100.60 mg |
| Sucrose | 25.75 mg |
| Hydroxypropylmethylcellulose | 12.85 mg |
| Separating layer | |
| Hydroxypropylmethylcellulose | 9.48 mg |
| Sucrose | 28.38 mg |
| Talc, 500 mesh | 50.45 mg |
| Enteric layer | |
| HPMCAS-LF | 66.78 mg |
| Triethyl citrate | 13.36 mg |
| Talc, 500 mesh | 20.01 mg |
| Finishing layer | |
| Color mixture white (HPMC + titanium dioxide) | 44.30 mg |
| HPMC | 11.09 mg |
| Talc | Trace |
| | 504.06 mg |

The product was made substantially according to the process used in Example 1 with the exception that the process was scaled up and initiated with 25 kg of sucrose starch non-pareils.

In more general terms, this invention provides a formulation as follows:

90 mg Fluoxetine base/capsule

| Bill of Materials | |
|---|---|
| Cores | |
| Sucrose - starch nonpareils, 30–35 mesh | 100–150 mg |
| Fluoxetine layer | |
| Fluoxetine hydrochloride | 100.5–100.8 mg |
| Sucrose | 20–30 mg |
| Hydroxypropylmethylcellulose | 10–15 mg |
| Separating layer | |
| Hydroxypropylmethylcellulose | 4–12 mg |
| Sucrose | 15–35 mg |
| Talc, 500 mesh | 25–60 mg |
| Enteric layer | |
| HPMCAS-LF | 60–90 mg |
| Triethyl citrate | 10–20 mg |
| Talc, 500 mesh | 15–25 mg |
| Finishing layer | |
| Color mixture white (HPMC + titanium dioxide) | 35–55 mg |
| HPMC | 5–15 mg |
| Talc | Trace |

Pellets made according to the above examples, and gelatin capsules filled with various batches of such pellets, have been thoroughly tested in the manners usual in pharmaceutical science. Results of stability tests show that the pellets and capsules have sufficient storage stability to be distributed, marketed and used in the conventional pharmaceutical manner.

Testing further shows that the pellets and capsules pass the conventional tests for enteric protection under conditions prevailing in the stomach. It has also been shown that the pellets release their load of fluoxetine acceptably quickly when exposed to conditions prevailing in the small intestine. Accordingly, the present invention has been demonstrated to solve the problems which previously were encountered in the formulation of other fluoxetine pellets.

The formulation of this invention can be used to treat people suffering from depression (including major depression (single episode, recurrent, melancholic), atypical, dysthymia, subsyndromal, agitated, retarded, co-morbid with cancer, diabetes, or post-myocardial infarction, involutional, bipolar disorder, psychotic depression, endogenous, and reactive), obsessive-compulsive disorder, or bulimia. In addition, the formulation can be used to treat people suffering from pain (given alone or in combination with morphine, codeine, or dextropropoxyphene), obsessive-compulsive personality disorder, post-traumatic stress disorder, hypertension, atherosclerosis, anxiety, anorexia nervosa, panic, social phobia, stuttering, sleep disorders, chronic fatigue, Alzheimer's disease, alcohol abuse, appetite disorders, weight loss, agoraphobia, improving memory, amnesia, smoking cessation, nicotine withdrawal syndrome symptoms, disturbances of mood and/or appetite associated with pre-menstrual syndrome, depressed mood and/or carbohydrate craving associated with pre-menstrual syndrome, disturbances of mood, disturbances of appetite or disturbances which contribute to recidivism associated with nicotine withdrawal, circadian rhythm disorder, borderline personality disorder, hypochondriasis, pre-menstrual syndrome (PMS), late luteal phase dysphoric disorder, pre-menstrual dysphoric disorder, trichotillomania, symptoms following discontinuation of other antidepressants, aggressive/intermittent explosive disorder, compulsive gambling, compulsive spending, compulsive sex, psychoactive substance use disorder, sexual disorder, schizophrenia, premature ejaculation, or psychiatric symptoms selected from stress, worry, anger, rejection sensitivity, and lack of mental or physical energy.

Although it will, of course, readily be understood that the amount of the fluoxetine actually to be administered will be determined by a physician, in the light of all the relevant circumstances including the condition to be treated, and the gender, weight, age, and other physical characteristics of the patient, many preferred regimens advocated for the above conditions involve the use of a 60 to 120 mg dose of fluoxetine. For example, it is not unusual for a patient to begin treatment at 20 mg/day for approximately two months, then switch to maintenance dosing at, e.g., 60–120 mg (especially 90 mg) once every week. Likewise, for treating, e.g., bulimia, a patient might start dosing at 60 mg/day, then later be maintained at 90–120 mg/week. The formulation of this invention allows the physician to prescribe, the pharmacist to supply, and the patient to obtain a single formulation capable of being used in different doses, either during initial titration of dose (e.g., increasing from 20 mg per day to 60 or 90 mg per day, or decreasing from 60 mg to 20 mg) or to later switch dosing regimens, e.g., from initial therapy to maintenance therapy.

In addition to the above capsules which comprise only fluoxetine as an active ingredient, a combination product of fluoxetine, particularly as the hydrochloride salt, may be made with pindolol as described in European Patent Application Publication 687,472. These active ingredients are generally present in the amounts of approximately 60–120 mg of fluoxetine hydrochloride and 1 to 60 mg of pindolol.

We claim:

1. A method of treating people suffering from depression, obsessive-compulsive disorder, bulimia, pain, obsessive-compulsive personality disorder, post-traumatic stress disorder, hypertension, atherosclerosis, anxiety, anorexia nervosa, panic, social phobia, stuttering, sleep disorders, chronic fatigue, Alzheimer's disease, alcohol abuse, appetite disorders, weight loss, agoraphobia, amnesia, smoking cessation, nicotine withdrawal syndrome symptoms, disturbances of mood and/or appetite associated with pre-menstrual syndrome, depressed mood and/or carbohydrate craving associated with pre-menstrual syndrome, disturbances of mood, disturbances of appetite or disturbances which contribute to recidivism associated with nicotine withdrawal, circadian rhythm disorder, borderline personality disorder, hypochondriasis, pre-menstrual syndrome (PMS), late luteal phase dysphoric disorder, pre-menstrual dysphoric disorder, trichotillomania, symptoms following discontinuation of antidepressants, aggressive/intermittent explosive disorder, compulsive gambling, compulsive spending, compulsive sex, psychoactive substance use disorder, schizophrenia, premature ejaculation, or pyschiatric symptoms selected from the group consisting of stress, worry, anger, rejection sensitivity, and lack of mental or physical energy without an increase in nausea comprising administering an enteric fluoxetine pellet comprising a) a core consisting of fluoxetine and one or more pharmaceutically acceptable excipients; b) an optional seperating layer comprising a non-reducing sugar; c) an enteric layer comprising hydroypropylmethylcellulose acetate succinate (HPMCAS) and one or more pharmaceutically acceptable excipients; d) an optional finishing layer.

2. A method of claim 1, employing a formulation containing 20–100 mg base equivalent of fluoxetine.

3. A method of claim 1 employing a formulation containing about 90 mg base equivalent of fluoxetine.

4. A method of claim 1 wherein the fluoxetine is present as fluoxetine hydrochloride.

5. A method of claim 2 wherein the fluoxetine is present as fluoxetine hydrochloride.

6. A method of claim 3 wherein the fluoxetine is present as fluoxetine hydrochloride.

7. A method of claim 1 employing a formulation containing the following:

| Cores | |
|---|---|
| Sucrose - starch nonpareils, 30–35 mesh | 100–150 mg |
| Fluoxetine layer | |
| Fluoxetine hydrochloride | 100.5–100.8 mg |
| Sucrose | 20–30 mg |
| Hydroxypropylmethylcellulose | 10–15 mg |
| Separating layer | |
| Hydroxypropylmethylcellulose | 4–12 mg |
| Sucrose | 15–35 mg |
| Talc, 500 mesh | 25–60 mg |
| Enteric layer | |
| HPMCAS-LF | 60–90 mg |
| Triethyl citrate | 10–20 mg |
| Talc, 500 mesh | 15–25 mg |
| Finishing layer | |
| Color mixture white (HPMC + titanium dioxide) | 35–55 mg |
| HPMC | 5–15 mg |
| Talc | Trace. |

8. A method of claim 1 of treating people suffering from pain, further comprising the coadministration of morphine, codeine, or dextropropoxyphene.

9. A method of claim 8 employing a formulation containing 20–100 mg base equivalent of fluoxetine.

10. A method of claim 8 employing a formulation containing about 90 mg base equivalent of fluoxetine.

* * * * *

UNITED STATES PATENT AND TRADEMARK OFFICE
CERTIFICATE OF CORRECTION

PATENT NO. : 5,985,322

DATED : November 16, 1999

INVENTOR(S) : Neil R. Anderson, Roger F. Harrison, Daniel F. Lynch and Peter L. Oren It is certified that an error appears in the above-identified patent and that said Letters Patent is hereby corrected as shown below:

Column 13, line 25 reads "...physical energy without an increase in nausea comprising..." should read --...physical energy without an increase in nausea or sexual dysfunction comprising...--

Signed and Sealed this

Seventeenth Day of April, 2001

Attest:

NICHOLAS P. GODICI

Attesting Officer     Acting Director of the United States Patent and Trademark Office

Disclaimer 5,985,322—Neil R. Anderson, West Lafayette; Roger F. Harrison, Zionsville; Daniel F. Lynch, Indianapolis; Peter L. Oren, Fishers, all of Indiana. METHOD FOR THE TREATMENT OF CNS DISORDERS. Patent dated November 16, 1999. Disclaimer filed February 1, 2002 by the assignee Eli Lilly and Company.

Hereby enters this disclaimer to all the claims of said patent
*(Official Gazette, August 13, 2002)*